US00PP16180P2

(12) United States Plant Patent
Miedema-Jorna

(10) Patent No.: US PP16,180 P2
(45) Date of Patent: Jan. 3, 2006

(54) **NEW GUINEA *IMPATIENS* PLANT NAMED 'TAMAR LAVENDER'**

(50) Latin Name: *Impatiens hawkeri*
Varietal Denomination: Tamar Lavender

(75) Inventor: Anita Miedema-Jorna, De Lier (NL)

(73) Assignee: Fides Goldstock Breeding B.V., DeLier (NL)

( * ) Notice: Subject to any disclaimer, the term of this patent is extended or adjusted under 35 U.S.C. 154(b) by 79 days.

(21) Appl. No.: 10/923,979

(22) Filed: Aug. 23, 2004

(51) Int. Cl.
*A01H 5/00* (2006.01)

(52) U.S. Cl. ..... Plt./318

(58) Field of Classification Search ..... Plt./318
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of New Guinea *Impatiens* plant named 'Tamar Lavender', characterized by its upright, broadly outwardly spreading and uniformly mounded plant growth habit; freely branching and freely flowering habit; very dark green-colored foliage; and large, rounded, light pink and red purple bi-colored flowers that are positioned above and beyond the foliage.

2 Drawing Sheets

Botanical classification/cultivar designation: *Impatiens hawkeri* cultivar Tamar Lavender.

BACKGROUND OF THE INVENTION

The present Invention relates to a new and distinct cultivar of New Guinea *Impatiens* plant, botanically known as *Impatiens hawkeri*, and hereinafter referred to by the name 'Tamar Lavender'.

The new *Impatiens* is a product of a planned breeding program conducted by the Inventor in De Lier, The Netherlands. The objective of the breeding program is to develop new *Impatiens* cultivars with an large rounded flowers with attractive foliage and flower coloration.

The new *Impatiens* originated from a cross-pollination made by the Inventor in 1998 with an unnamed proprietary seedling selection of *Impatiens hawkeri*, not patented, as the female, or seed, parent with the *Impatiens hawkeri* cultivar Papete, disclosed in U.S. Plant Pat. No. 8,457, as the male, or pollen, parent. The cultivar Tamar Lavender was discovered and selected by the Inventor as a flowering plant within the progeny of the stated cross-pollination in a controlled environment in De Lier, The Netherlands.

Asexual reproduction of the new cultivar by terminal cuttings in De Lier, The Netherlands since 1999, has shown that the unique features of this new *Impatiens* are stable and reproduced true to type in successive generations.

SUMMARY OF THE INVENTION

The following traits have been repeatedly observed and are determined to be the unique characteristics of 'Tamar Lavender'. These characteristics in combination distinguish 'Tamar Lavender' as a new and distinct *Impatiens* cultivar:

1. Upright, broadly outwardly spreading and uniformly mounded plant growth habit.
2. Freely branching and freely flowering habit.
3. Very dark green-colored foliage.

4. Large, mounded, light pink and red purple bi-colored flowers that are positioned above and beyond the foliage.

Plants of the new *Impatiens* can be compared to plants of the female parent selection. In side-by-side comparisons conducted by the Inventor in De Lier, The Netherlands, plants of the new *Impatiens* differed from plants of the female parent selection in the following characteristics:

1. Plants of the new *Impatiens* and the female parent selection differed in leaf coloration as plants of the female parent selection had green-colored foliage.
2. Plants of the new *Impatiens* and the female parent selection differed in flower coloration as plants of the female parent selection had red purple-colored flowers.

Plants of the new *Impatiens* can be compared to plants of the male parent, the cultivar Papete. In side-by-side comparisons conducted by the Inventor in De Lier, The Netherlands, plants of the new *Impatiens* differed from plants of the cultivar Papete in the following characteristics:

1. Plants of the new *Impatiens* and and the cultivar Papete differed in leaf coloration as plants of the cultivar Papete had green-colored foliage.
2. Plants of the new *Impatiens* and the cultivar Papete differed in flower coloration as plants of the cultivar Papete had red purple-colored flowers.

Plants of the new *Impatiens* can also be compared to plants of the cultivar Tamar Violet, not patented. In side-by-side comparisons conducted by the Inventor in De Lier, The Netherlands, plants of the new *Impatiens* differed from plants of the cultivar Tamar Violet in the following characteristics:

1. Plants of the new *Impatiens* and the cultivar Tamar Violet differed in leaf coloration as plants of the cultivar Tamar Violet had lighter green-colored foliage.
2. Plants of the new *Impatiens* and the cultivar Tamar Violet differed in flower coloration as plants of the cultivar Tamar Violet had purple-colored flowers.

Plants of the new *Impatiens* can also be compared to plants of the cultivar Tamar Light Lavender, not patented. In side-by-side comparisons conducted by the Inventor in De Lier, The Netherlands, plants of the new *Impatiens* differed from plants of the cultivar Tamar Light Lavender in the following characteristics:

1. Plants of the new *Impatiens* and the cultivar Tamar Light Lavender differed in leaf coloration as plants of the cultivar Tamar Light Lavender had lighter green-colored foliage.
2. Plant of the new *Impatiens* had larger and more rounded flowers than plants of the cultivar Tamar Light Lavender.
3. Plant of the new *Impatiens* and the cultivar Tamar Light Lavender differed in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Impatiens*.

The photograph on the first sheet comprises a side perspective view of a typical flowering plant of 'Tamar Lavender' grown in a container.

The photograph on the second sheet is a close-up view of typical flowers of 'Tamar Lavender'.

DETAILED BOTANICAL DESCRIPTION

The cultivar Tamar Lavender has not been observed under all possible environmental conditions. The phenotype may vary somewhat with variations in environment such as temperature and light intensity, without, however, any variance in genotype.

The aforementioned photographs, following observations and measurements describe plants grown in De Lier, The Netherlands, under commercial production practice in a glass-covered greenhouse. Rooted young plants were planted in 12-cm containers and the aformentioned photograph and following observations and measurements were taken about eight to ten weeks later in June. During the production of the plants, day and night temperatures were about 18 to 20° C. In the following description, color references are made to The Royal Horticultural Society Colour Chart, 2001 Edition, except where general terms of ordinary dictionary significance are used.

Botanical classification: *Impatiens hawkeri* cultivar Tamar Lavender.

Parentage:

*Female parent.*—Unnamed proprietray seedling selection of *Impatiens hawkeri*, not patented.

*Male parent.*—*Impatiens hawkeri* cultivar Papete, disclosed in U.S. Plant Pat. No. 8,457.

Propagation:

*Type cutting.*—Terminal tip cuttings.

*Time to initiate roots.*—Summer: About 5 to 7 days at 19 to 20° C. Winter: About 6 to 8 days at 19 to 20° C.

*Time to produce a rooted cutting.*—Summer: About 14 to 19 days at 19 to 20° C. Winter: About 14 to 21 days at 19 to 20° C.

*Root description.*—Numerous, thin, and freely branching; white to brown in color.

Plant description:

*General appearance.*—Upright, broadly outwardly spreading and uniformly mounded plant growth habit; freely branching habit; bushy appearance; freely flowering. Moderately vigorous.

*Crop time.*—From a rooted cutting, about 12 weeks are required to produce finished flowering plants in 12-cm containers.

*Plant height.*—About 22 cm.

*Plant diameter or spread.*—About 47 cm.

*Lateral branches.*—Quantity per plant: About 15. Length: About 14.4 cm. Diameter: About 7 mm. Internode length: About 5.5 cm. Strength: Moderate. Texture: Smooth, glabrous. Luster: Glossy. Color: 144A to 144B.

*Foliage description.*—Arrangement: Primarily in whorls with about four leaves per whorl; simple. Length: About 12.4 cm. Width: About 5.1 cm. Shape: Elliptic. Apex: Apiculate. Base: Attenuate. Margin: Serrulate with ciliation. Texture, upper and lower surfaces: Smooth, glabrous. Luster, upper surface: Dull. Luster, lower surface: Somewhat glossy. Venation pattern: Pinnate. Color: Developing foliage, upper surface: 147A. Developing foliage, lower surface: Between 187A and 187B. Fully expanded foliage, upper surface: Between 139A and much darker than 147A. Fully expanded foliage, lower surface: Slightly lighter than 187A. Venation, upper surface: 187B to 187C. Venation, lower surface: 187B. Petiole: Length: About 4.1 cm. Diameter: About 3.5 mm. Texture: Smooth, glabrous. Color, upper surface: 182B. Color, lower surface: Between 185A and 187B.

Flower description:

*Flower type and flowering habit.*—Single, rounded, light pink and red purple bi-colored flowers. Freely and continuously flowering; usually about 13 flowers and flower buds per lateral branch. Flowers positioned above and beyond the foliage; flowers typically face upright to outward, typically parallel to the leaf canopy. Petals not persistent; gynoecium persistent. Flowers not fragrant.

*Flower longevity.*—Flowers last about ten days on the plant.

*Flowering season.*—Year-round under greenhouse conditions. In the garden, plants flower from the spring throughout the summer.

*Flower buds.*—Length: About 1.6 cm. Diameter: About 1 cm. Shape: Ovoid. Color: 183A.

*Flower diameter.*—About 6.8 cm.

*Flower depth* (*excluding spur*).—About 1.8 cm.

*Petals.*—Quantity: Five per flower, imbricate. Length: Banner petals: About 3.8 cm. Lateral and base petals: About 3.3 cm. Width: Banner petals: About 5.2 cm. Lateral and base petals: About 4.6 cm. Shape: Broadly obcordate. Apex: Emarginate. Base: Attenuate. Margin: Entire. Aspect: Mostly flat. Texture, upper and lower surfaces: Smooth, glabrous; satiny. Color: When opening, banner petal, upper surface: 76C to 76D; central blotch, 67B. When opening, lateral and base petals, upper surface: 76C to 76D; basal spot, 67B. When opening, banner petal, lower surface: 77C to 77D; central blotch, 60A. When opening, lateral and base petals, lower surface: 77C to 77D; basal spot, between 61A and 67A. Fully opened, banner petal, upper surface: 76D; central blotch, 67B. Fully opened, lateral and base petals, upper surface: 76C to 76D; basal spot, 67C. Fully opened, banner petal, lower surface: N74C; central blotch, 53B. Fully opened, lateral and base petals, lower surface: N74C; basal spot, 67A.

*Spur.*—Length: About 5.9 cm. Diameter: At apex: About 0.5 mm. At flower: About 1.5 mm. Aspect: Curved. Color, immature and mature: 144B.

*Peduncles.*—Length: About 6.2 cm. Diameter: About 2 mm. Texture: Smooth, glabrous. Strength: Moderately strong, flexible. Angle: About 50° from vertical. Color: 144B.

*Reproductive organs.*—Androecium: Stamen number: Five fused at anthers, hooded; filaments free. Anther length: About 4 mm. Anther shape: Obovate. Anther color: 157A. Pollen amount: Moderate. Pollen color: 155D. Gynoecium: Pistil quantity: One per flower. Pistil length: About 1 mm. Stigma color: 58A. Style: Not visible. Ovary: Five-celled. Ovary color: 146A; towards the apex, 183A to 183B.

*Seed/fruit.*—Seed and fruit development has not been observed.

Disease/pest resistance: Plants of the new *Impatiens* have not been obseved to be resistant to pathogens and pests common to *Impatiens.*

Temperature tolerance: Plants of the new *Impatiens* have been observed to tolerate temperatures of 10° C. to 35° C.

It is claimed:

1. A new and distinct cultivar of New Guinea *Impatiens* plant named 'Tamar Lavender', as illustrated and described.

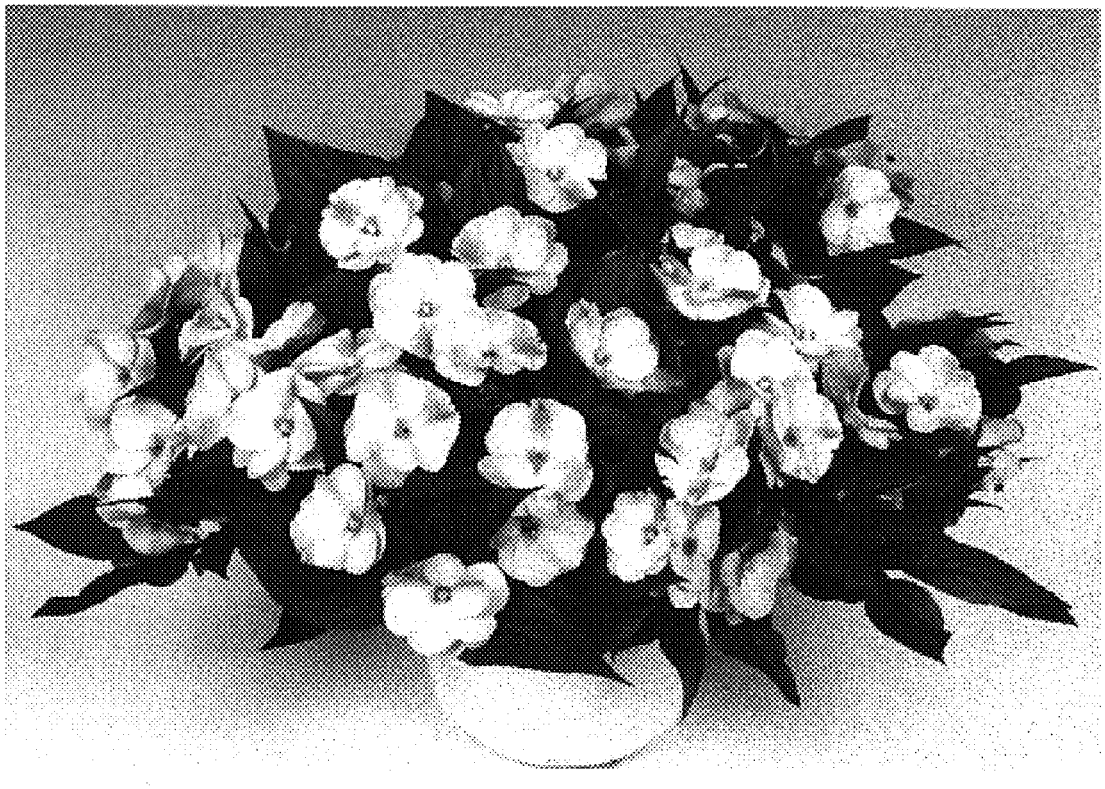

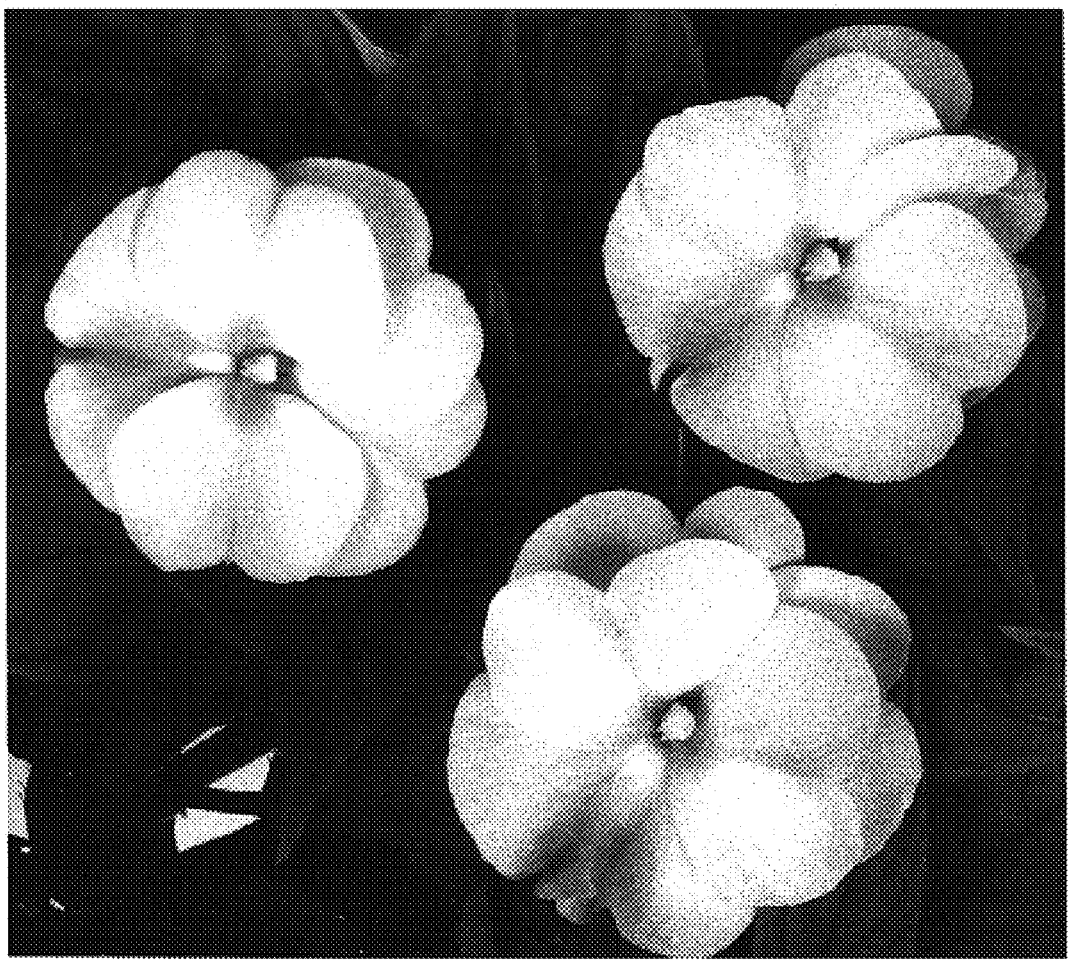

* * * * *